United States Patent
Subramani et al.

(10) Patent No.: US 10,131,589 B2
(45) Date of Patent: Nov. 20, 2018

(54) PROCESS FOR SIMULTANEOUS PRODUCTION OF ALCOHOLS AND OLIGOMER PRODUCT FROM HYDROCARBON FEED STOCK

(71) Applicant: Indian Oil Corporation Limited, Bandra (East), Mumbai (IN)

(72) Inventors: Saravanan Subramani, Haryana (IN); Reshmi Manna, Haryana (IN); Pushkar Varshney, Haryana (IN); Anju Chopra, Haryana (IN); Debasis Bhattacharyya, Haryana (IN); Brijesh Kumar, Haryana (IN); Biswapriya Das, Haryana (IN); Ravinder Kumar Malhotra, Haryana (IN)

(73) Assignee: INDIAN OIL CORPORATION LIMITED, Bandra (East) (IN)

( * ) Notice: Subject to any disclaimer, the term of this patent is extended or adjusted under 35 U.S.C. 154(b) by 518 days.

(21) Appl. No.: 14/727,307

(22) Filed: Jun. 1, 2015

(65) Prior Publication Data

US 2015/0344383 A1 Dec. 3, 2015

(30) Foreign Application Priority Data

May 31, 2014 (IN) .................. 1807/MUM/2014

(51) Int. Cl.
| | | |
|---|---|---|
| *C07C 29/04* | (2006.01) | |
| *C07C 2/08* | (2006.01) | |
| *C10L 1/06* | (2006.01) | |
| *C10L 1/16* | (2006.01) | |
| *C10L 10/10* | (2006.01) | |
| *C07C 2/28* | (2006.01) | |
| *C10G 50/00* | (2006.01) | |
| *C10L 1/02* | (2006.01) | |
| *B01J 35/06* | (2006.01) | |
| *B01J 35/10* | (2006.01) | |

(52) U.S. Cl.
CPC ............... *C07C 2/08* (2013.01); *B01J 35/065* (2013.01); *B01J 35/1009* (2013.01); *B01J 35/1014* (2013.01); *B01J 35/1061* (2013.01); *C07C 2/28* (2013.01); *C07C 29/04* (2013.01); *C10G 50/00* (2013.01); *C10L 1/02* (2013.01); *C10L 1/06* (2013.01); *C10L 1/16* (2013.01); *C10L 10/10* (2013.01); *C07C 2531/08* (2013.01); *C10G 2400/02* (2013.01); *C10L 1/1608* (2013.01); *C10L 2200/0423* (2013.01); *C10L 2270/023* (2013.01)

(58) Field of Classification Search
None
See application file for complete search history.

(56) References Cited

U.S. PATENT DOCUMENTS

| | | |
|---|---|---|
| 3,351,635 A | 11/1967 | Kollar |
| 4,100,220 A | 7/1978 | Bowman et al. |
| 8,067,655 B2 | 11/2011 | Nichols et al. |
| 2007/0083069 A1 | 4/2007 | Candela et al. |

FOREIGN PATENT DOCUMENTS

| | | | |
|---|---|---|---|
| EP | 1074534 | 2/2001 | |
| WO | WO03/020666 | * 3/2003 | ............... C07C 2/02 |
| WO | 03/033442 | 4/2003 | |
| WO | 2010/065234 | 6/2010 | |

* cited by examiner

*Primary Examiner* — Ana Z Muresan
(74) *Attorney, Agent, or Firm* — Workman Nydegger

(57) ABSTRACT

The present invention relates to a process for production of oligomer products from olefinic C4 feed stocks comprising isobutene, butenes, butanes, butadienes and mixture thereof. Particularly, the present invention relates to a process for the preparation of oligomers using olefinic C4 feed stock in presence of tertiary butyl alcohol (TBA) and iso propyl alcohol (IPA).

11 Claims, 3 Drawing Sheets

PROCESS FOR SIMULTANEOUS PRODUCTION OF ALCOHOLS AND OLIGOMER PRODUCT FROM HYDROCARBON FEED STOCK

FIELD OF THE INVENTION

The present invention relates to a process for production of oligomer products from olefinic C4 feed stocks comprising isobutene, butenes, butanes, butadienes and mixture thereof. Particularly, the present invention relates to a process for the preparation of oligomers using olefinic C4 feed stock in presence of tertiary butyl alcohol (TBA) and iso propyl alcohol (IPA).

BACKGROUND OF THE INVENTION

Oligomerization of light olefins is a well-known process which utilizes different catalytic system for production of various desired end products. Oligomerization of isobutene particularly dimerization of isobutene is important for production of high octane gasoline blending component. Dimerization of isobutene is a well-known side reaction in the MTBE production process and highly exothermic. In order to avoid the formation of dimer, methanol is always kept in excess to the stoichiometric ratio required for MTBE production. By reducing the methanol to isobutene mole ratio one can produce both the dimer product and MTBE in the same reactor.

EP 1074534 utilizes similar kind of process as MTBE production, which adds fresh methanol, MTBE, MSBE, secondary butyl alcohol and mixture thereof at different mole ratios along with the refinery C4 feedstock containing isobutene to the reactor employing an oligomerization catalyst. As there are more number of alcohols and ethers added as fresh feedstock the cost for production of dimer product will grow up and it will affect the economics of the process when comes into the industrial application point of view.

In oligomerization reaction using ion exchange resin as catalyst, particularly in dimerization of isobutene to isooctene, various polar compounds are used as selectivity enhancer for dimer product. Tertiary butyl alcohol (TBA) is one such polar component widely used in the dimerization process as selectivity enhancer.

TBA is one of the costliest chemicals which is produced commercially through well-known Oxirane process as described in U.S. Pat. No. 3,351,635. Some of the patents like U.S. Pat. No. 8,067,655, WO03/033442 made the efforts to recover the alcohol especially TBA using the energy intensive and cost intensive process like extraction, dual distillation etc. as the TBA cannot be recovered easily owing to its azeotrope formation with water.

In situ production of TBA in a dimerization reactor as disclosed in U.S. Pat. No. 4,100,220, WO 2010/065234, will make the progress of both the reaction competitive and yield undesired product selectivity w.r.t TBA and dimer. This is because both the reactions require different reaction environment which cannot be maintained in a single reactor.

US 2007/0083069 describes a process for selective oligomerization of isobutene to di-isobutene in presence of TBA as selectivity enhancing modifier. The said modifier is prepared in a separate reactor and the substantially free of water modifier is separated and sent to oligomerization reactor where isobutene reacts in the presence of said separated modifier to selectively form di-isobutene. No clear description for the method of separation of the modifier has been given in this application.

Abbreviations and Definitions

TBA—Tertiary butyl alcohol;
IPA—Isopropyl Alcohol;
TMP-1—244, Tri Methyl Pentene-1;
TMP-2—244, Tri Methyl Pentene-2;
MTBE—Methyl Tertiary Butyl ether.
FCC—Fluid Catalytic Cracking
RON—Research Octane Number In the context of present invention, Dimer means the product of C4 feedstock iso-olefin oligomerization process, limited to dimerization, which comprises mainly isooctene, combination of 2,4,4, TMP-1 and 2,4,4 TMP-2, which is also called as di-isobutylene. Dimer also comprises the product from co-dimerization reaction i.e the reaction between isobutene and n-butenes like 5,5 dimethyl hexene, 2,5 dimethyl 3-hexene, 3,4 dimethyl-2-hexene etc.

Trimer means the product of C4 feedstock iso-olefin oligomerization process, limited to trimerization process, which mainly comprises tri-isobutylene present in the form of 2,2,4,6,6-pentamethyl heptene-1 and 2,2,4,6,6-pentamethyl heptene-2. Similar to dimers, trimers also exist within various isomeric forms like 2,2,4,6,6-pentamethyl heptene-3 etc.

SUMMARY OF THE INVENTION

The present invention relates to a process for production of oligomer products from olefinic C4 feed stocks comprising isobutene, butenes, butanes, butadienes and mixture thereof. Particularly, the present invention relates to a process for the preparation of oligomers using olefinic C4 feed stock in presence of tertiary butyl alcohol (TBA) and iso propyl alcohol (IPA).

The present invention also relates to a process for continuous and consistent production of a mixture of alcohols from olefinic feed stocks, which comprises the hydrocarbons having carbon number in the range of C3-C12. In a preferred aspect, the feed stock comprises propylene, iso butene and mixture thereof.

In another aspect of the present invention, TBA, IPA, other alcohols such as secondary butyl alcohol are produced simultaneously in a separate hydration reaction zone where the reaction environment is conducive for the production of alcohols free of water with maximum selectivity, eliminating the need of external addition of TBA & other alcohols and thereby making the process an economically attractive one. Entire catalyst in the hydration reaction zone is maintained in wet form, with always same level of wetting so as to maximize the selectivity of TBA, IPA and other alcohols such as secondary butyl alcohol. Also, the alcohols are produced at a continuous and consistent rate by maintaining constant wetting of catalyst in the hydration reaction zone. As the TBA, IPA and other alcohols are produced in a separate zone of hydration reactors with more control over the reaction to produce alcohols as required in the oligomerization zone, the additional step for recovery of excess alcohols is eliminated in the present invention, which makes the process an economically attractive one. As the TBA, IPA and other alcohols produced in the hydration reaction zone is directly routed to oligomerization reaction zone, the need for heating the TBA and the associated problems are also solved in the present invention. The main advantage of the invention is that TBA, IPA and other alcohols produced in the hydration reaction zone are free of water and do not require any separation step for recovery of anhydrous alcohols. Moreover, there is no requirement of adding multiple alcohols and ethers from external source for improving the selectivity of the dimer product in the present invention. The methanol added in the said prior art gets consumed immediately by reacting with isobutene to form MTBE leading to continuous buildup of MTBE in the composite product and the same is required to be removed at least as a purge stream, which in turn makes the downstream recovery section a complicated one.

In another aspect of the present invention, the TBA, IPA and other alcohols produced in the separate hydration reaction zone is partly routed to oligomerization reaction zone connected in series configuration to the hydration reaction zone. The hydration process is operated at olefin space velocity in the range of 2 to 10 hr-1, temperature in the range of 60-100° C., Pressure in the range of 12 to 20 bar.

The oligomerization of C4 feedstock comprising isobutene is performed by reacting a C4 feedstock comprising isobutene and a mixture comprising tertiary butyl alcohol and iso propyl alcohol in an oligomerization reaction zone in the presence of a catalyst to obtain dimers. The mole percentage of IPA in the mixture of IPA and TBA is varied from 10 to 90%. The oligomerization process is operated at olefin space velocity in the range of 2 to 10 hr$^{-1}$, temperature in the range of 40-100° C., Pressure in the range of 8 to 16 bar.

The dimers obtained by the process of the present invention are used to mix with a gasoline pool comprising Heavy Reformate in the range of 25-55 wt %, Isomerate in the range 10-35 wt %, FCC gasoline in the range of 10-40 wt % and Naphtha in the range of 0-10 wt % to form a composite gasoline composition to improve the octane number. The amount of dimer used to prepare composite gasoline composition is in the range of 0.5 to 6 wt % of the composite gasoline composition.

Further, the present invention provides a process for production of trimers by feeding a first portion of a C4 feedstock comprising isobutene, propylene and water to a hydration reaction zone to produce a product comprising tertiary butyl alcohol and iso propyl alcohol, and feeding a second portion of the C4 feedstock comprising isobutene to an oligomerization reaction zone.

Feeding a portion of the product obtained after hydration to the oligomerization reaction zone, and oligomerizing the C4 feedstock comprising isobutene in the presence of a catalyst to produce an effluent comprising dimers, fractionating the effluent into a fraction comprising dimers and recycling a portion of said fraction comprising dimers into the hydration reaction zone, to obtain a product comprising tertiary butyl alcohol, iso propyl alcohol, C8 alcohols and unconverted dimers. Feeding a portion of the product obtained after recycling to the oligomerization reaction zone to obtain trimers.

The amount of water is added in such a way that, it is equal to or less than the moisture holding capacity of the catalyst. The main advantage of the invention is that it does not require any separation step for recovery of anhydrous alcohol. Also, the alcohols are produced at a constant rate by maintaining constant wetting of catalyst in the hydration reaction zone. As the catalyst is maintained in a constant wetting, many of the side reactions are eliminated in the hydration reaction zone. A portion of the composite alcohol mixture from hydration reaction zone is routed to oligomerization reaction zone as selectivity modifier. The composite alcohol mixture increases the selectivity of dimer product in oligomerization reaction zone (9).

Any kind of conventional reactors like plug flow reactor, continuous stirred tank reactor, fluidized bed reactor, bubble column reactor, etc. can be used in both the reaction zone.

Figure 1:
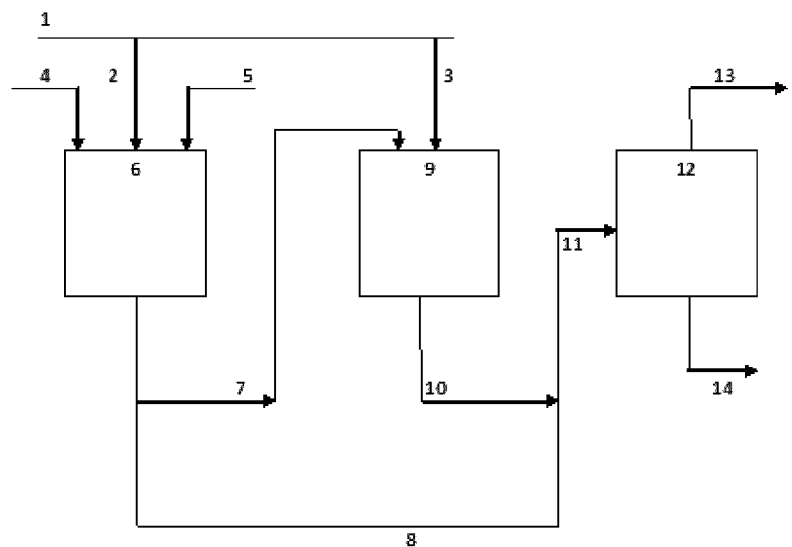
FIG. 1: A process for production of oligomer products from olefinic C4 feed stocks is described wherein, C4 feed stock comprising isobutene (1) as one of the component is divided into two portions (2) & (3) and routed to the hydration reaction zone (6) and oligomerization reaction zone (9) respectively. The ratio of feed to (6) and (9) varies from 0.01 to 0.8. Propylene feed (4) enters only in the reaction zone (6) in the proportion of 1 to 20 wt % to the C4 feed stock (2). Water (5) preferably DM water else any water free of metals and poisons eg; steam condensate can be added to the hydration reaction zone (6) for hydration of the respective olefins. Water is added in a quantity which is less than or equal to the moisture holding capacity of the catalyst present in the reaction zone so as to maintain always the same percentage wetting of the catalyst. In particular it should be in the range of 70-90% of moisture holding capacity of the catalyst. This in turn helps in maintaining constant yield of alcohols through hydration reaction in hydration reaction zone (6), thereby maintaining the ratio of alcohols to isobutene at the inlet of oligomerization reaction zone (9). The product from the reaction zone (6) is further divided into two streams (7) and (8), stream (7) along with the produced iso propyl alcohol, tertiary butyl alcohol and unconverted propylene and butylenes enters into the oligomerization reaction zone (9). Stream (8) which combines with the product (10) of reactor (9) enters into zone 12 which is a fractionating column for separation of products. Products are separated into two different cuts, Stream (13) comprises lighter components which has true boiling point less than 25° C., Stream (14) has true boiling point higher than 25° C. The unconverted propylene from reaction zone (6) is partially converted to respective dimer product in reaction zone (9).
Figure 2:
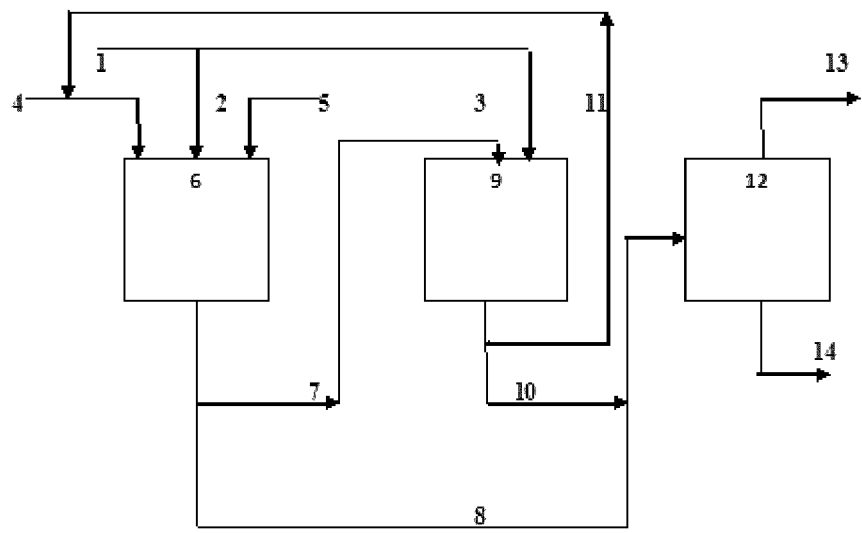

FIG. 2: A process for production of oligomer products from olefinic C4 feed stocks is described wherein C4 feed stock comprising isobutene (1) as one of the component is divided into two portions (2) & (3) and routed to the hydration reaction zone (6) and oligomerization reaction zone (9) respectively. The ratio of feed to (6) and (9) varies from 0.01 to 0.8. Propylene feed (4) enters only in the reaction zone (6) in the proportion of 1 to 20 wt % to the C4 feed stock (2). Water (5) preferably DM water else any water free of metals and poisons eg; steam condensate can be added to the reaction zone (6) for hydration of the respective olefins. Water is added in a quantity which is less than or equal to the moisture holding capacity of the catalyst present in the reaction zone so as to maintain always the same percentage wetting of the catalyst. This in turn helps in maintaining constant yield of alcohols through hydration reaction in hydration reaction zone (6), the product from the hydration reaction zone (6) is further divided into two streams (7) and (8), and stream (7) along with the produced iso propyl alcohol, tertiary butyl alcohol and unconverted propylene and butylenes enters into the oligomerization reaction zone (9).

The product from the oligomerization reaction zone (9) is further divided into two streams (10) and (11); Stream (10) combines with stream (8) and enters into zone (12) which is a fractionating column for separation of products. Products are separated into two different cuts, Stream (13) comprises lighter components which has true boiling point less than 25° C., Stream (14) has true boiling point higher than 25° C. A purge stream (11) which is a product from reaction zone (9) is recycled back to reaction zone (6) for hydration reaction and to increase the yield of alcohols by increasing the temperature.

The advantage of the invention is, it increases the conversion of olefins by increasing the inlet temperature of the hydration reaction zone and advantageously it also forms the heavier alcohol which in turn increases the selectivity of Trimer product in the oligomerization reaction zone (9). The trimer product can be used as fuel additive, in the production of neo-acids etc.

The amount of recycle of product is in the range of 25-75 wt % of total fresh feed and the mole ratio of isobutene to iso octene (dimer) at the inlet of oligomerization zone is in the range of 1:1 to 5:1. Yield of C8 alcohols is in the range of 0.5 to 2.5 wt %. The unconverted dimer from hydration reaction zone enters into the oligomerization zone where it reacts with C4 feedstock comprising isobutene and produces trimer. Increased yield of C3, C4 alcohols and the formation of C8 alcohols in the hydration zone favors the production of trimer in the oligomerization zone.

Figure 3:
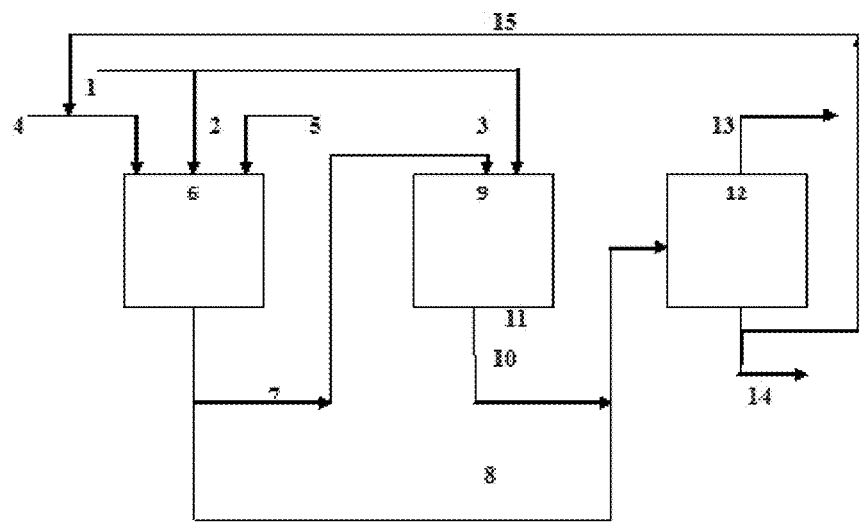

FIG. 3: A process for production of oligomer products from olefinic C4 feed stocks is described wherein, C4 feed stock comprising isobutene (1) as one of the component is divided into two portions (2) & (3) and routed to the hydration reaction zone (6) and oligomerization reaction zone (9) respectively. The ratio of feed to (6) and (9) varies from 0.01 to 0.8. Propylene feed (4) enters only in the hydration reaction zone (6) in the proportion of 1 to 20 wt % to the C4 feed stock (2). Water (5) preferably DM water else any water free of metals and poisons eg; steam condensate can be added to the hydration reaction zone (6) for hydration of the respective olefins. Water is added in a quantity which is less than or equal to the moisture holding capacity of the catalyst present in the reaction zone so as to maintain always the same percentage wetting of the catalyst. This in turn helps in maintaining constant yield of alcohols through hydration reaction in the reaction zone (6). The product from the reaction zone (6) is further divided into two streams (7) and (8), stream (7) along with the produced iso propyl alcohol, tertiary butyl alcohol and unconverted propylene and butylenes enters into the reaction zone (9).

Stream (8) which combines with the product (10) of reaction zone (9) enters into zone 12 which is a fractionating column for separation of products. Products are separated into two different cuts, Stream (13) comprises lighter components which has true boiling point less than 25° C., Stream (14) has true boiling point higher than 25° C.

A purge stream (15) is taken from stream (14) and recycled back to the hydration reaction zone (6) for production of heavier alcohols and to suppress the formation of heavier oligomers (Tetramers) in reaction zone (9).

The amount of recycle of product is in the range of 25-75 wt % of total fresh feed and the mole ratio of isobutene to iso octene (dimer) at the inlet of oligomerization zone is in the range of 1:1 to 5:1. Yield of C8 alcohols is in the range of 0.5 to 2.5 wt %. The unconverted dimer from hydration reaction zone enters into the oligomerization zone where it reacts with C4 feedstock comprising isobutene and produces trimer. Increased yield of C3, C4 alcohols and the formation of C8 alcohols in the hydration zone favors the production of trimer in the oligomerization zone.

Figure 4:
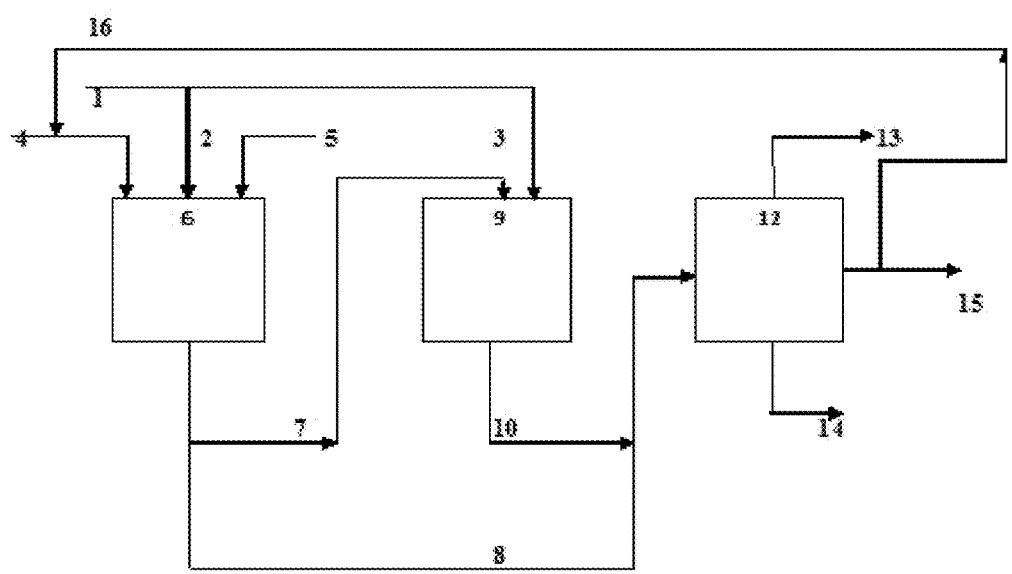

FIG. 4: A process for production of oligomer products from olefinic C4 feed stocks is described wherein, C4 feed stock comprising isobutene (1) as one of the component is divided into two portions (2) & (3) and routed to the hydration reaction zone (6) and oligomerization reaction zone (9) respectively. The ratio of feed to (6) and (9) varies from 0.01 to 0.8. Propylene feed (4) enters only in the hydration reaction zone (6) in the proportion of 1 to 20 wt % to the C4 feed stock (2). Water (5) preferably DM water else any water free of metals and poisons eg; steam condensate can be added to the reaction zone (6) for hydration of the respective olefins. Water is added in a quantity which is less than or equal to the moisture holding capacity of the catalyst present in the hydration reaction zone so as to maintain always the same percentage wetting of the catalyst. This in turn helps in maintaining constant yield of alcohols through hydration reaction in reaction zone (6), the product from the reaction zone (6) is further divided into two streams (7) and (8), and stream (7) along with the produced iso propyl alcohol, tertiary butyl alcohol and unconverted propylene and butylenes enters into the oligomerization reaction zone (9).

Stream (8) which combines with the product (10) of the oligomerization reaction zone (9) enters into zone (12) which is a fractionating column for separation of products. Products are separated into three different cuts, Stream (13) comprises lighter components which has true boiling point less than 25° C. Stream (14) has true boiling point higher than 105° C. Stream (15) has true boiling point in the range of 25° C. to 105° C.

A purge stream (16) is taken from stream (15) which is a concentrated dimer product which comprises >98% purity dimer product is recycled back to the hydration reaction zone (6) for production of C8 alcohols which further suppresses the formation of heavier oligomers (Tetramer) in reaction zone (9).

The amount of recycle of product is in the range of 25-75 wt % of total fresh feed and the mole ratio of isobutene to iso octene (dimer) at the inlet of oligomerization zone is in the range of 1:1 to 5:1. Yield of C8 alcohols is in the range of 0.5 to 2.5 wt %. The unconverted dimer from hydration reaction zone enters into the oligomerization zone where it reacts with C4 feedstock comprising isobutene and produces trimer. Increased yield of C3, C4 alcohols and the formation of C8 alcohols in the hydration zone favors the production of trimer in the oligomerization zone.

Figure 5:
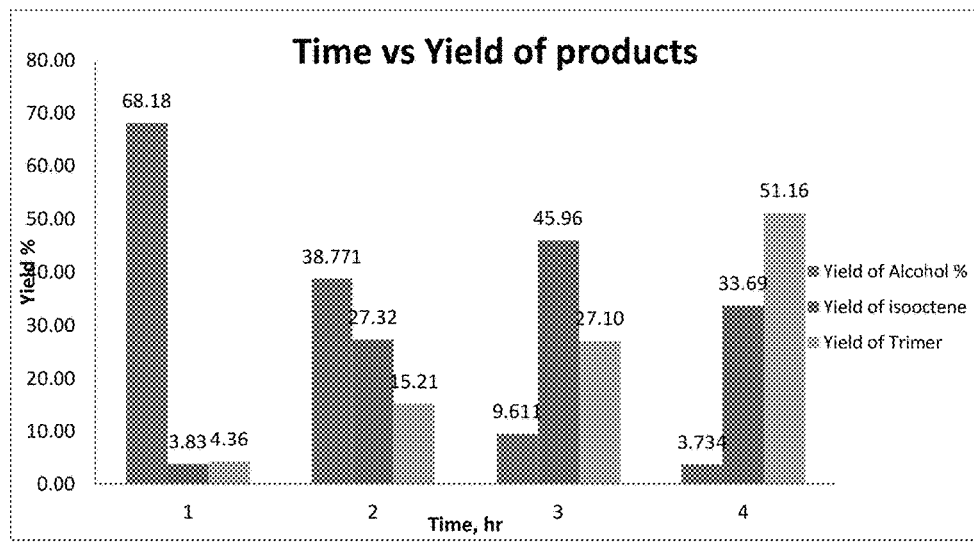

FIG. 5: Shows the effect on the yield of products due to change in catalyst wetting with time.

Figure 6:
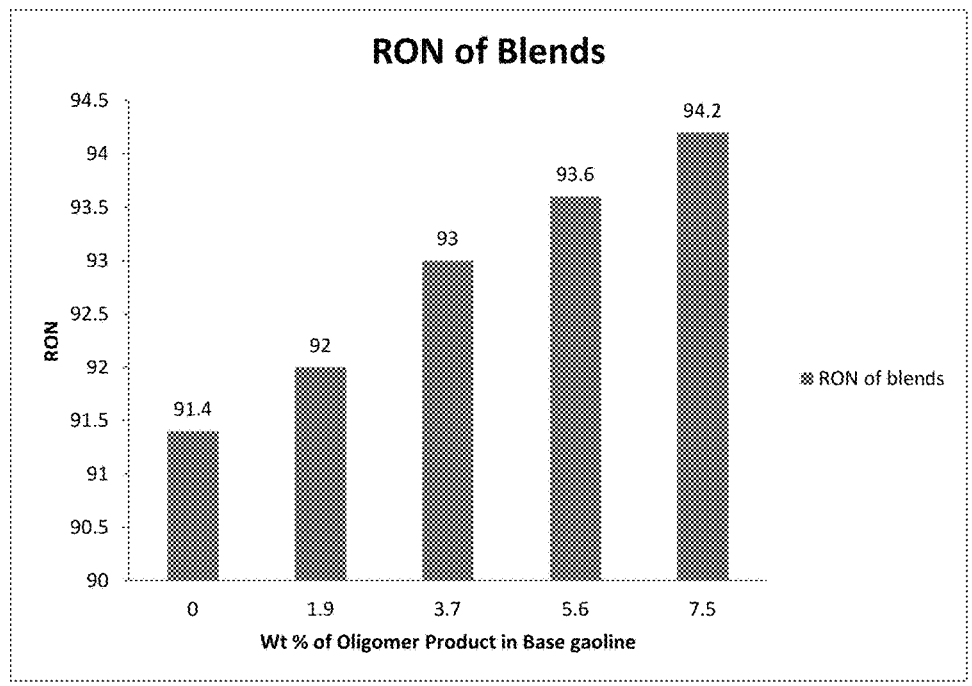

FIG. 6: Shows the effect of blending oligomer product in the gasoline pool on RON.

DETAILED DESCRIPTION OF THE INVENTION

The present invention discloses a process for production of oligomer products which mainly comprises dimer and trimer product of isobutene; using acidic catalyst including ion exchange resin catalyst in a multiple reactor system from olefinic C4 feed stocks comprising isobutene, butenes, butanes, butadienes and mixture thereof. Particularly, the present invention discloses a process for the preparation of oligomers using olefinic C4 feed stock in presence of tertiary butyl alcohol (TBA) and iso propyl alcohol (IPA).

The present invention also discloses a process for continuous and consistent production of a mixture of alcohols from olefinic feed stocks which comprises the hydrocarbons having carbon number in the range of C3-C12. In a preferred aspect, the feed stock comprises propylene, iso butene and mixture thereof.

In accordance with the present invention, light olefinic hydrocarbon feedstock is contacted with acidic catalysts including ion exchange resin catalysts in two different reaction zones, which are connected in parallel-series configuration and operating at different conditions specifically to favor the production of TBA, IPA, other alcohols such as secondary butyl alcohol and heavier alcohols (C8+), in the first reaction zone and the oligomerization in the second reaction zone.

The feed to the process is the C4 feed stream which comprises isobutene as one of the component which is available from any of the refinery process units like FCC, Naphtha cracker, Delayed Coker, isobutane dehydrogenation etc. In addition to the above, the feed also comprises propylene as the feedstock with a minimum purity of 70 wt %. The propylene can be obtained from any of the process like FCC, delayed coker, Naphtha cracking and propane dehydrogenation etc. The C4 feedstock also contains n-butane, isobutane, n-butenes, 1, 3 butadiene etc. The propylene feedstock also contains propane and propadiene.

Two different catalysts are used in the hydration reactor and the oligomerization reactor, respectively. The catalyst used in the hydration reactor has the minimum moisture holding capacity of 40 to 65 wt % of the catalyst. The catalyst is a polymer based cation exchange resin which has the concentration of acid sites less than 5 eq/kg, most preferably less than 4 eq/kg and surface area less than 40 $m^2/g$ and average pore diameter of less than 250 Å.

The catalyst used in the oligomerization reactor is a polymer based cation exchange resin which has the concentration of acid sites greater than 5 eq/kg and surface area greater than 40 $m^2/g$ and average pore diameter greater than 250 Å and has the minimum divinely benzene content of 20 wt % to 85 wt % of the catalyst.

Accordingly, the present invention provides a process for iso-olefin oligomerization, the process comprising:
  feeding a C4 feedstock comprising isobutene to an oligomerization reaction zone,
  feeding a product comprising tertiary butyl alcohol and iso propyl alcohol to the oligomerization reaction zone, and
  oligomerizing the C4 feedstock comprising isobutene in the presence of a catalyst to produce dimers.

In an aspect of the present invention, the product comprising tertiary butyl alcohol and iso propyl alcohol are obtained by a process comprising:
  a. feeding propylene, a C4 feed stock comprising isobutene, and water to a hydration reaction zone; and
  b. conducting hydration of the C4 feed stock and propylene, in the presence of a hydration catalyst to obtain a product comprising tertiary butyl alcohol and iso propyl alcohol.

In yet another aspect of the present invention, the product comprising tertiary butyl alcohol and iso propyl alcohol are obtained simultaneously in the said hydration reaction zone and a portion of the product comprising tertiary butyl alcohol and iso propyl alcohol is transferred to the oligomerization reaction zone.

In still another aspect of the present invention, the yield of dimer is obtained in the range of 60-78 wt % with the dimer selectivity of more than 90%.

In one other aspect of the present invention, the process for continuous and consistent production of a mixture of alcohols, the process comprising:
  a. feeding an olefinic feed stock and water to a hydration reaction zone; and
  b. conducting hydration of the olefinic feed stock in the presence of a catalyst in the hydration reaction zone, wherein the constant percentage wetting of the catalyst is up to 90% of its moisture holding capacity, to obtain a consistent yield of the mixture of alcohols.

In yet another aspect of the present invention, the olefinic feedstock comprises the hydrocarbons having carbon number in the range of C3-C12.

In still another aspect of the present invention, the olefinic feedstock is selected from C4 feedstock comprising isobutene, propylene, or a mixture thereof.

In further another aspect of the present invention, the C4 feed stock comprises isobutene, butenes, butanes, butadienes and mixture thereof.

In another aspect of the present invention, the propylene feedstock also contains propane.

In further another aspect of the present invention, the propylene is 1 to 20 wt % of the C4 feed stock.

In still another aspect of the present invention, the percentage wetting of the catalyst in the hydration reaction zone is maintained in the range of 70-90% of moisture holding capacity of the catalyst.

In further another aspect of the present invention, the water in the hydration reaction zone is added in the range of 14 to 19 wt % of feed.

In still another aspect of the present invention, the product obtained in hydration reaction zone comprises tertiary butyl alcohol, iso propyl alcohol, secondary butyl alcohol and other C4 alcohols.

In a further aspect, the present invention provides a process for producing trimers, the process comprising:
  (a) feeding a first portion of a C4 feedstock comprising isobutene, propylene and water to a hydration reaction zone to produce a product comprising tertiary butyl alcohol and iso propyl alcohol,
  (b) feeding a second portion of the C4 feedstock comprising isobutene to an oligomerization reaction zone,
  (c) feeding a portion of the product obtained in step (a) to the oligomerization reaction zone, and oligomerizing the C4 feedstock comprising isobutene in the presence of a catalyst to produce an effluent comprising dimers,
  (d) fractionating the effluent into a fraction comprising dimers,
  (e) recycling a portion of said fraction comprising dimers into the hydration reaction zone, to obtain a product comprising tertiary butyl alcohol, iso propyl alcohol, C8 alcohols and unconverted dimers,
  (f) feeding a portion of the product obtained in step (e) to the oligomerization reaction zone to obtain trimers.

In a preferred aspect of the present invention, the amount of dimer recycled in step (e) in the process of producing trimer, is in the range of 25-75 wt % of fresh feed. In further preferred aspect, the fraction comprising dimers obtained in step (d) comprises >90% dimers. In another preferred aspect of the present invention, the catalyst used in the hydration reaction zone is a polymer based cation exchange resin having the concentration of acid sites less than 5 eq/kg, surface area less than 40 $m^2/g$ and average pore diameter of less than 250 Å. In another aspect, the catalyst used in the oligomerization reaction zone is a polymer based cation exchange resin having concentration of acid sites greater than 5 eq/kg, surface area greater than 40 $m^2/g$, average pore diameter greater than 250 Å and divinyl benzene content of 20 to 85 wt %.

In still another aspect of the present invention, the present invention provides a composite gasoline composition comprising:

0.5 to 7.5 wt % of the oligomerised product obtained by the process of the present invention, and a gasoline pool comprising heavy reformate in the range of 25-55 wt %, Isomerate in the range 10-35 wt %, FCC gasoline in the range of 10-40 wt % and Naphtha in the range of 0-10 wt %.

In a preferred aspect, the composite gasoline composition of the present invention has an improved octane number by 0.5-2.8.

In another aspect of the present invention, the ratio of the C4 feed stream to the hydration reaction zone and oligomerization reaction zone is 0.01 to 0.8.

In another aspect of the present invention, the effluent from the oligomerization reaction zone is fractionated into two cuts, lighter components which have true boiling point less than 25° C. and true boiling point higher than 25° C.

In another aspect of the present invention, the effluent from the oligomerization reaction zone is fractionated into three different cuts, lighter components which has true boiling point less than 25° C., component having true boiling point in the range of 25° C. to 105° C. and a component having true boiling point higher than 105° C.

In accordance with the present invention, the ratio of first portion of C4 feed stream to the second portion of C4 feed stream is 0.01 to 0.8 and the propylene feed is in a proportion of 1 to 20 wt % of the first portion of the C4 feed stream. Water used in the hydration reaction is free of metals and poisons. In accordance with the present invention, water is added in the hydration reaction zone in an amount which is less than or equal to the moisture holding capacity of the catalyst. A constant percentage wetting of the catalyst in the range of 70-90% of moisture holding capacity of the catalyst is maintained to obtain constant yield of alcohols in first reaction zone (hydration zone). The product/alcohols obtained in hydration reaction zone comprise iso propyl alcohol, butyl alcohol, heavier alcohols (C8+) and unconverted propylene and butylenes.

Having described the basic aspects of the present invention, the following non-limiting examples illustrate specific embodiment thereof.

Example 1

Variation in Yield of Products Due to Change in Catalyst Wetting with Time 10 g of Hydration Catalyst is soaked with water in the range of 100% of moisture holding capacity of the catalyst and loaded in the tubular reactor; Feed comprising 90 wt % of isobutene and 10 wt % of propylene is passed through the reactor at 65° C. and at a pressure of 16 bar. The products from the reactor is separated and analyzed for the detailed hydrocarbon analysis after every 1 hr. It is found from FIG. 5 that with time the yield of tertiary butyl alcohol and iso propyl alcohol decreased whereas the dimer and trimer product increased. This clearly shows that the water present in the catalyst reacts with propylene and isobutene in feed to form iso propyl and tertiary butyl alcohol and as the water gets consumed, i.e. wetting of catalyst is reduced with time, the formation of dimer (isooctene) and trimer is dominant. It is to be noted that there is no addition of water after the catalyst loading through any means inside the reactor. It is also found that 50 wt % of water which is present in the catalyst is consumed within 1 hr operation and the remaining 50 wt % of water is consumed throughout the remaining 3 hrs of operation. Hence it is clear that the catalyst wetting is required to be maintained in particular percentage for continuous and consistent production of alcohols with time, without presence of excess water in the reactor effluent stream.

Example 2

Effect of Wetting of the Catalyst on TBA Yield

It is clear from example-1 that the selectivity and yield of the desired products depend upon the amount of water present in the catalyst, hence it is desired to find out the effect of wetting of catalyst on the yield of TBA only, to establish the proof of concept. A batch stirred tank reactor is used for this purpose and then 10 g of catalyst is loaded in each experiment with 50 wt % wetting, 70 wt % wetting and 90 wt % wetting. 27 g of isobutene is charged in each batch along with n-hexane as a diluent. Reaction has been carried out at 16 bar pressure and at 65° C. Nitrogen is used as inert for pressurization. Reaction time given is 15 min. The results are tabulated as shown below:

TABLE 1

| | % wetting | | |
|---|---|---|---|
| | 50 | 70 | 90 |
| Conversion of Isobutene, wt % | 75.14 | 60.53 | 55.26 |
| TBA Yield (On Water + Isobutene), wt % | 34.30 | 37.77 | 48.58 |
| Selectivity of TBA, % | 42.2 | 61.5 | 91.3 |
| Selectivity to oligomers, % | 57.8 | 38.5 | 8.7 |

From the above table it is clear that with the increase in % wetting of catalyst the selectivity of TBA increases whereas the conversion of isobutene decreases. It is seen that with increased amount of water content in the catalyst, although the conversion of isobutene is getting reduced, the selectivity to TBA is increasing leading to overall higher yield of TBA. Beyond 90% wetting traces of water found in the product. Hence it is desired to maintain the wetting of catalyst less than or equal to 90%, more specifically in the range of 70-90%.

Example 3

Effect of Wetting of the Catalyst on TBA Yield in Continuous Mode

In order to establish the yield and selectivity of TBA which corroborates to 90% wetting of catalyst in continuous mode, requisite quantity of catalyst is loaded in tubular reactor and the olefin space velocity is maintained at 2 hr$^{-1}$, pressure and temperature are maintained at 16 bar and 65° C. respectively. Effect of water percentage in total feed has been studied and the results are shown below:

TABLE 2

| | Run No. | | | |
|---|---|---|---|---|
| | 1 | 2 | 3 | 4 |
| Water in feed, wt % | 8.2 | 14.5 | 18.7 | 18.7 |
| Conversion of Isobutene, wt % | 54.93 | 41.48 | 40.38 | 40.56 |
| TBA Yield, wt % | 8.23 | 24.21 | 51.12 | 50.9 |
| Isooctene Yield, wt % | 21.34 | 18.9 | 1.93 | 1.97 |
| Trimer Yield, wt % | 27.7 | 6.66 | 0 | 0 |

It is clear from the above table that increase in water content increase the TBA yield and decreases the oligomer product yield. TBA yield almost closely matches with 90 wt % wetting results of Example 2. Hence the feed is continued for 150 hrs operation at the Run No 3 condition to check whether the TBA yield is continuous and consistent. It is observed that even after 150 hrs of operation, the yield of TBA is consistent and there is either no degradation or any improvement, which is shown in Run No 4. Also it is observed that there is no water present in the product, which clearly shows that the anhydrous alcohol including TBA can be produced with consistent yield and without any separation step by maintaining the percentage wetting of catalyst in a particular proportion. The water which is injected after 90% wetting of catalyst on continuous basis gets totally consumed for production of TBA and other alcohols and thereby avoiding its slippage to oligomerization zone.

Example 4

Effect of Temperature on Alcohol Yield During Recycle of Oligomer Product

In order to find out the effect of increase in the conversion of isobutene and yield of TBA, temperature has been increased from 65 to 75° C. by feeding the preheated pure iso-octene feed at the elevated temperature so as to maintain the inlet temperature of the hydration reaction zone at 75° C. and found that there is an increase in yield from 51.12 wt % to 70.59 wt %. This shows that increase in temperature in the range of 65 to 75 will increase the conversion as well as yield of TBA.

TABLE 3

|  | Run No | |
| --- | --- | --- |
|  | 1 | 2 |
| Temperature, ° C. | 65 | 75 |
| Water in feed, wt % | 18.7 | 18.7 |
| Conversion of Isobutene, wt % | 40.38 | 64.26 |
| TBA Yield, wt % | 51.12 | 70.59 |
| Isooctene Yield, wt % | 1.93 | 0 |
| Trimethyl Pentanol Yield, wt % | 0.72 | 1.96 |
| Trimer Yield, wt % | 0 | 0 |

It is evident from the above example that purge stream recycle of oligomer product either from oligomerization zone bottom or from fractionating column bottom or from the middle cut of fractionators will increase the inlet temperature of hydration reactor (As the temperature of recycle streams are higher than the fresh feed stream) thereby increasing the yield of alcohols. It is also seen that there is a formation of heavier alcohols (C8 alcohol) during the recycle operation in hydration reaction zone.

Example—5

Effect of Methanol to Isobutene Mole Ratio on MTBE and Isooctene Selectivity

This example illustrates that if methanol and isobutene are processed in the oligomerization reactor, by varying the methanol to isobutene mole ratio one can produce isooctene and MTBE simultaneously using the same oligomerization catalyst. The reaction has been carried out in tubular reactor system at 8 bar and at 4.35 $hr^{-1}$ isobutene space velocity. The results obtained are shown below:

TABLE 4

| Run No. | Methanol to isobutene Mole ratio | Actual Avg. temp | % conversion of isobutene | MTBE selectivity on isobutene basis | 2,4,4, TMP-1 selectivity | 2,4,4, TMP-2 selectivity | Total Isooctene selectivity |
| --- | --- | --- | --- | --- | --- | --- | --- |
| 1 | 0.78 | 41 | 78.74 | 36.07 | 3.95 | 1.03 | 4.98 |
| 2 | 0.75 | 60 | 86.64 | 56.97 | 2.21 | 0.57 | 2.78 |
| 3 | 0.75 | 81 | 70.10 | 66.81 | 3.11 | 0.00 | 3.11 |
| 4 | 0.48 | 41 | 74.78 | 39.81 | 7.82 | 0.09 | 7.91 |
| 5 | 0.48 | 62 | 85.14 | 53.98 | 6.62 | 1.70 | 8.32 |
| 6 | 0.48 | 80 | 81.46 | 51.04 | 11.99 | 3.12 | 15.11 |
| 7 | 0.24 | 41 | 77.18 | 31.37 | 21.04 | 5.39 | 26.43 |
| 8 | 0.27 | 60 | 82.82 | 8.84 | 28.17 | 7.39 | 35.57 |
| 9 | 0.24 | 80 | 87.49 | 21.14 | 26.79 | 7.29 | 34.09 |

It is seen from the above table that when methanol to isobutene mole ratio is reduced from 0.7 to 0.2 the selectivity to isobutene increases and it is clear that the both Methyl Tert Butyl Ether (MTBE) and Isooctene co-exist when methanol is used as a polar component, hence with the use of methanol one cannot increase the yield and selectivity of isooctene owing to the reaction of methanol with isobutene to form MTBE.

Example 6

Effect of Selectivity and Yield of Isooctene when Only TBA is Used as Additive

The feed which is used in the following experiments has the composition as shown in the following Table:

TABLE 5

| C4 composition (wt %) | |
| --- | --- |
| I-Butane | 30.04 |
| n-Butane | 11.04 |
| Iso-Butene | 18.73 |
| Trans-2-Butene | 13.2 |
| Cis-2-Butene | 10.15 |
| 1-Butene | 16.17 |
| 1,3 Butadiene | 0.93 |

10 g of dried oligomerization catalyst has been loaded in the tubular reactor, the reactor system comprises gas feed module, liquid feed module with C3/C4 feed injection in the liquid form into the reactor in precisely controlled manner through high pressure pumps, additionally two liquids such as additives can be pumped into the reactor. At the downstream of the reactor two stage separation system enables the gas liquid separation. In the first stage heavier liquid products can be separated and in the second stage, lighter liquid products can be separated and recycled back to the reactor system.

TABLE 6

| Run No. | Temperature (actual), °C. | Pressure, bar | Isobutene space velocity, h$^{-1}$ | Wt % of TBA on total C4 feed | % conversion of isobutene | Total isooctene selectivity | Total isooctene yield on IC4 = basis |
|---|---|---|---|---|---|---|---|
| 1 | 80 | 8 | 0.635 | 0.594 | 91.55 | 31.76 | 29.08 |
| 2 | 83 | 12 | 1.288 | 1.0907 | 85.51 | 45.74 | 39.11 |
| 3 | 81 | 8 | 3.687 | 0.247 | 62.43 | 79.22 | 49.46 |
| 4 | 80.5 | 8 | 1.995 | 0.347 | 73.65 | 63.37 | 46.67 |
| 5 | 80 | 8 | 3.830 | 0.5206 | 53.30 | 70.69 | 37.68 |
| 6 | 64 | 8 | 1.990 | 0.3718 | 35.60 | 70.52 | 25.11 |
| 7 | 80 | 8 | 3.862 | 0.3718 | 69.75 | 78.06 | 54.45 |
| 8 | 102 | 8 | 1.990 | 0.3718 | 94.03 | 43.23 | 40.65 |

Experiments have been conducted in the above mentioned system in tubular reactor on continuous mode operation. Only Tertiary butyl alcohol is used as additive under different operating condition as mentioned in the above Table. Increase in reaction temperature and decrease in space velocity leads to undesired reaction there by reducing the selectivity and yield of isooctene, It is clearly seen that the maximum selectivity and yield of isooctene could not be increased beyond 79% and 54 wt % respectively while using only TBA as additive for dimerization purpose.

Example 7

Combined Effect of Iso Propyl Alcohol and TBA on Iso-Octene Selectivity and Yield

TABLE 7

| Run No. | Temperature (actual), °C. | Pressure, bar | Isobutene space velocity, hr$^{-1}$ | IPA + TBA on total C4 feed, wt % | % conversion of isobutene | Total isooctene selectivity, % | Total isooctene yield, Wt % |
|---|---|---|---|---|---|---|---|
| 1 | 79 | 8 | 1.975 | 1.367 | 93.05 | 52.82 | 49.15 |
| 2 | 80 | 8 | 1.994 | 1.352 | 97.80 | 48.00 | 46.95 |
| 3 | 80 | 8 | 1.995 | 2.35 | 83.35 | 91.80 | 76.52 |
| 4 | 81 | 8 | 1.980 | 2.32 | 79.57 | 92.50 | 73.60 |
| 5 | 78 | 8 | 1.994 | 3.28 | 67.45 | 93.80 | 63.27 |
| 6 | 81 | 8 | 1.992 | 3.29 | 65.32 | 94.20 | 61.53 |

Mixture of iso propyl alcohol and Tertiary butyl alcohol which is produced in hydration reactor is passed through tubular reactor system under varying operating conditions. It is seen that in combination of iso propyl alcohol and tertiary butyl alcohol selectivity of isooctene increased beyond 90%. It is conventionally known that the selectivity of isooctene cannot be increased without sacrificing conversion of isobutene. Due to this lower conversion of isobutene, the overall yield of isooctene decreases even at higher selectivity. However, in the present invention, it is observed surprisingly that combined use of iso propyl alcohol and tertiary butyl alcohol in oligomerization reactor significantly increases both yield and selectivity of dimer product, when compared to the yield and selectivity of using only tertiary butyl alcohol (Example—6). In order to check the consistent yield each experiment has been repeated with 24 hrs interval time in continuous operation mode. It is seen that consistent yield and selectivity observed in both the cases.

Example 8

Effect of Blending Oligomer Product in the Gasoline Pool

The product as obtained in Example—7 which comprises oligomer product with greater than 90% dimer selectivity is blended in various proportions in the base gasoline pool which comprises 34.46 wt % heavy reformate, 35.2 wt % FCC gasoline and 30.35 wt % isomerate to obtain a composite gasoline composition with improved characteristics of Research Octane Number (RON) as shown in FIG. 6.

It is observed clearly from the figure that with increase in blending percentage of oligomer product from 1.9 to 7.5 wt % the RON of composite gasoline increases from 91.4 to 94.2

The above example represents one of the uses of the oligomer product as fuel component, however it can also be used in various other products such as alkyl phenol, surfactants etc.

The major advantages of the present invention are as follows:

The main advantage of the present invention is production of alcohols and oligomer product and the flexibility of maintain the selectivity of the product according to the need which in turn based on the economics.

Another advantage of the invention is that the alcohol which is required for maintaining the selectivity of the dimer/trimer product is produced internally using the same feedstock which is used for oligomerization.

Yet another advantage of the process is, it does not require any separation step for recovery of anhydrous alcohol. Also, the alcohols are produced at a constant rate by maintaining constant wetting of catalyst in the hydration reaction zone. As the catalyst is maintained in a constant wetting, many of the side reactions are eliminated in the hydration reaction zone.

Further advantage of the present invention is the production of mixture of alcohol at constant rate in hydration reaction zone which increases both selectivity and yield of the dimer product in oligomerization zone to greater than 90% and 70% respectively.

Yet another advantage of the present invention is that the recycle of oligomer product from reactor bottom to the inlet of hydration zone increases inlet temperature of hydration zone feed which further increases the yield of alcohols in hydration zone.

Further advantage of the invention is that recycle of oligomer product especially iso-octene in hydration zone forms Trimethyl Pentanol in the range of 0.5-2.5 wt %, which is a C8 alcohol.

Yet another advantage of the present invention is that the recycle of dimer product in hydration zone which in turn enters into oligomerization zone where the selectivity and yield of trimer product increases.

We claim:

1. A process for iso-olefin oligomerization, the process comprising:
    feeding a C4 feedstock comprising isobutene to an oligomerization reaction zone;
    feeding a mixture of alcohols to the oligomerization reaction zone; and
    oligomerizing the C4 feedstock comprising isobutene in the presence of an oligomerization catalyst to produce dimers,
    wherein the mixture of alcohols is obtained in a first reaction zone a hydration zone operated at different conditions and catalysts, by:
    (a) feeding an olefinic feedstock and water to the hydration reaction zone, wherein the water is added in a range of 14 to 19 wt % of feed; and
    (b) conducting hydration of the olefinic feed stock in the presence of a hydration catalyst in the hydration reaction zone, wherein the constant percentage wetting of the hydration catalyst is maintained in the range of 70-90% of moisture holding capacity of the catalyst, to obtain a consistent yield of the mixture of alcohols which is directly routed to the oligomerization reaction zone.

2. The process as claimed in claim 1, wherein the yield of dimer is obtained in the range of 60-78 wt % with the dimer selectivity of >90%.

3. The process as claimed in claim 1, wherein the olefinic feedstock comprises the hydrocarbons having carbon number in the range of C3-C12.

4. The process as claimed in claim 3, wherein the olefinic feedstock is selected from C4 feedstock comprising isobutene, propylene, or a mixture thereof.

5. The process as claimed in claim 1, wherein the C4 feedstock comprises isobutene, butenes, butanes, butadienes and mixture thereof.

6. The process as claimed in claim 1, wherein the product obtained in hydration reaction zone comprises tertiary butyl alcohol, iso propyl alcohol, secondary butyl alcohol and other C4 alcohols.

7. The process as claimed in claim 1, the process further comprising:
    fractionating the effluent into a fraction comprising dimers;
    recycling a portion of said fraction comprising dimers into the hydration reaction zone, to obtain a product comprising tertiary butyl alcohol, iso propyl alcohol, C8 alcohols and unconverted dimers; and
    feeding a portion of the product obtained to the oligomerization reaction zone to obtain trimers.

8. The process of claim 7, wherein the amount of dimer recycled is in the range of 25-75 wt % of fresh feed.

9. The process of claim 7, wherein the fraction comprising dimers comprises >90% dimers.

10. The process as claimed in claim 1, wherein the catalyst used in the hydration reaction zone is a polymer based cation exchange resin having the concentration of acid sites less than 5 eq/kg, surface area less than 40 $m^2/g$ and average pore diameter of less than 250 Å.

11. The process as claimed in claim 1, wherein the catalyst used in the oligomerization reaction zone is a polymer based cation exchange resin having concentration of acid sites greater than 5 eq/kg, surface area greater than 40 $m^2/g$, average pore diameter greater than 250 Å and divinyl benzene content of 20 to 85 wt %.

* * * * *